(12) United States Patent
Murphy

(10) Patent No.: US 6,790,219 B1
(45) Date of Patent: Sep. 14, 2004

(54) FILTER WITH INTEGRATED OBTURATOR TIP AND METHODS OF USE

(75) Inventor: Richard O. Murphy, Sunnyvale, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 236 days.

(21) Appl. No.: 10/013,229

(22) Filed: Nov. 6, 2001

(51) Int. Cl.[7] ............................................. A61M 29/00
(52) U.S. Cl. ...................................................... 606/200
(58) Field of Search ................................ 606/200, 113, 606/127, 194

(56) References Cited

U.S. PATENT DOCUMENTS

| | | | |
|---|---|---|---|
| 5,681,347 A | * | 10/1997 | Cathcart et al. ............ 606/200 |
| 5,846,260 A | | 12/1998 | Maahs |
| 5,951,585 A | | 9/1999 | Cathcart et al. |
| 6,007,557 A | | 12/1999 | Ambrisco et al. |
| 6,511,497 B1 | * | 1/2003 | Braun et al. ................. 606/200 |

FOREIGN PATENT DOCUMENTS

WO    WO 01/34228 A1    5/2001

* cited by examiner

*Primary Examiner*—(Jackie) Tan-Uyen T. Ho
(74) *Attorney, Agent, or Firm*—John Christopher James; O'Melveny & Myers

(57) ABSTRACT

An endoluminal device having an elongate tubular member and a filter slideably received within a lumen of the tubular member. An obturator tip is carried by the filter and shaped to rest against the distal end of the elongate tubular member when the filter is within the lumen of the tubular member. Methods of using the obturator and the introducer for introducing the filter into a vessel, such as an aorta, are also disclosed.

24 Claims, 4 Drawing Sheets

FILTER WITH INTEGRATED OBTURATOR TIP AND METHODS OF USE

FIELD OF THE INVENTION

The present invention generally relates to the field of embolic protection, and more particularly to endoluminal devices that can be used to provide embolic protection during a surgical procedure.

BACKGROUND OF THE INVENTION

During various cardiothoracic, pulmonary, and vascular surgeries, including coronary artery bypass grafting, heart valve repair or replacement, atrial or ventricular septal defect repair, angioplasty, atherectomy, aneurysm repair, and pulmonary thrombectomy, or any other procedure that makes use of cardiopulmonary bypass, cannulation of a patient's vessel(s) are often required to provide vascular access for delivery of various diagnostic and therapeutic devices. In a conventional approach, incisions generally made by a surgical blade are needed for introduction of medical device(s). For example, during coronary artery bypass grafting (CABG) surgeries, cardiopulmonary bypass is established by cannulation of the aorta to provide circulatory isolation of the heart and coronary blood vessels. Multiple incisions on the aorta may be required, i.e., one for insertion of the arterial cannula, another for insertion of a balloon occluder to provide coronary isolation from the peripheral vascular system, and another for insertion of an arterial filter to provide protection against distal embolization. Once the incisions are made on the aorta, the devices often remain in the aorta throughout the entire procedure despite only being used intermittently, e.g., the cardioplegia catheter.

Due to significant mortality and morbidity associated with the conventional CABG surgeries from the use of cardiopulmonary bypass for circulatory support and the traditional method of access by median sternotomy, minimally invasive concepts recently have been adopted to make cardiothoracic procedures less invasive. Minimally invasive alternatives include the minimally invasive direct CABG procedure in which the operation is performed through minimal access incisions, eliminating cardiopulmonary bypass. The second alternative is to perform the procedure through minimal access incisions, and cardiopulmonary support is instituted through an extra-thoracic approach, i.e., the port access approach. The third alternative is to perform the procedure on a beating heart which allows greater access for more extensive revascularization, i.e., the "off pump" sternotomy approach. In any of the minimally invasive alternatives, the space allowed for multiple incisions and device insertion is limited.

The disadvantages associated with the conventional or minimally invasive approach are that (1) the current methods require bulky valves and plastic housings that interfere with a surgeon's working space, thereby reducing the space available for the surgeon to perform procedures, and (2) the aorta is traumatized as a result of multiple incisions, which may result in aortic dissection, aortic wall hematoma, and/or embolization of calcium plaque from the aortic wall. The greater the aortic trauma, the higher the perioperative morbidity a patient will endure.

Accordingly, there is a need for devices and methods which provide access to a vessel or body cavity and allow introduction of medical instrument(s), such as an arterial filter, through a single incision with minimal blood loss and with maximum convenience for the physician.

SUMMARY OF THE INVENTION

The present invention provides a medical device for introducing a blood filter into a body tissue, such as a vessel, or cardiac tissue, for preventing distal embolization. Obturators are also provided for a traumatic insertion through an incision in body tissue.

In a first embodiment, the medical device comprises an elongate tubular member having a lumen between a proximal end and a distal end. A filter, having an obturator tip at its distal end, is slideably received within the lumen of the elongate tubular member. The obturator tip is shaped to rest against the distal end of the elongate tubular member when the filter is within the lumen of the elongate tubular member. The filter is capable being advanced distally beyond the distal end of the elongate tubular member after the device is inserted into a vessel. A distal region of the elongate tubular member may include a suture flange for securing the device onto a vessel. The proximal end of the elongate tubular member may include a hemostatic valve to minimize blood loss.

In another embodiment, the elongate tubular member is flexible, thereby allowing a physician to manipulate the device in crowded surgical space. The filter comprises an expansion frame having an attached filter mesh that is generally conical. The obturator tip is attached at the apex of the conical mesh. The obturator tip, which may be made of thermoplastic polymer, silicone, urethane, or other suitable material, may be olive-shaped or star-shaped. The expansion frame, which comprises a generally circular ring of a flexible material, e.g., nitinol, may be attached to an elongate member that extends through the lumen of the elongate tubular member, e.g., hypotube. An optional cantilever beam bisects the generally circular ring and attaches to the ring at a distal end.

In a first method of using the obturators and introducers described above for introduction of a blood filter, the filter is contracted and withdrawn into the lumen of the elongate tubular member so that the obturator tip rests against the distal end of the elongate tubular member. The obturator tip and the distal end of the elongate tubular member are inserted into a blood vessel, e.g., an aorta, after an incision is made on the vessel wall. A hemostatic valve mounted within the lumen of the introducer prevents blood loss. In certain embodiments, a suture flange is provided on the distal end of the introducer, and sutures can be placed on the flange to stabilize the device onto the body tissue. The filter and the obturator tip are then advanced beyond the distal end of the elongate tubular member. The filter is deployed in the vessel to prevent embolization of materials, such as atheromatous plaque, thrombus, or tissue debris generated during the procedure. Vascular surgeries, including coronary artery bypass grafting, heart valve repair or replacement, atrial or ventricular septal defect repair, angioplasty, atherectomy, aneurysm repair, and pulmonary thrombectomy, can then be performed after establishment of cardiopulmonary bypass. After completion of the surgical procedure, the filter and the captured embolic debris are withdrawn into the lumen of the elongate tubular member. The device is then removed from the vessel.

There are several advantages in using the device disclosed herein for performing arterial filtration during vascular surgeries. For example, the devices (1) are constructed of fewer parts, thereby allowing easy manipulation of the device, (2) are less bulky, thereby allowing the ease of use in a crowded surgical space, (3) have less manufacturing cost, (4) have a flexible delivery system that allows added flexibility for working in a limited space, (5) have a reduced outer diameter as compared with an introducer sheath adapted to receive a length of hypotube that carries a filter, and (6) eliminate the step of removing a separate obturator during use (a step that can cause blood loss).

Additional features of the present invention will become apparent from consideration of the following description taken in conjunction with the accompanying drawings.

DETAILED DESCRIPTION

Figure 1A:
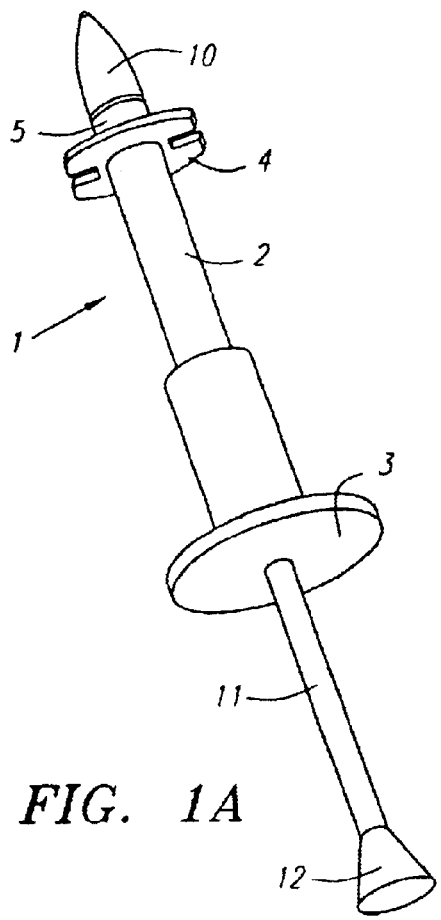
FIG. 1A depicts the medical device having a filter with obturator tip according to one embodiment of the invention.

A filter for use in a surgical procedure to prevent distal embolization is depicted in FIG. 1A. Device 1 includes tubular member 2 (e.g., a hypotube) having a proximal end, distal end 5, and a lumen that extends from the proximal to the distal end. The proximal end terminates proximally in handle 3 having finger grips as a handle for the operator. Suture flange 4 is shown near distal end 5 of tubular member 2.

Elongate member 11 is slideably received through the lumen of tubular member 2. Elongate member 11 is typically a tubular member having a lumen that communicates proximally with porous plug 12, which allows venting of air but not fluid or blood. Obturator tip 10 is shown in FIG. 1A seated against distal end 5 of tubular member 2.

Figure 1B:
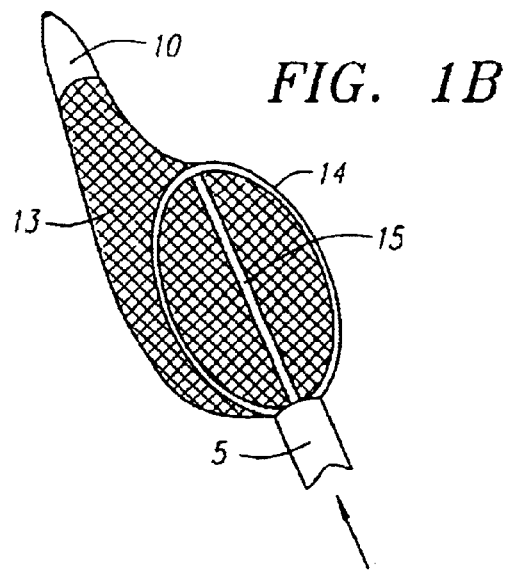
FIG. 1B depicts the device of FIG. 1A with filter deployed.

In use, elongate member 11 slideably advances to deploy the filter as shown in FIG. 1B. Filter 13 is carried by expansion frame 14, typically a wire frame constructed of nitinol material. Cantilever beam 15 slideably extends from elongate member 11 at distal end 5 of tubular member 2. The cantilever beam stabilizes expansion frame 14 and acts as a frame sizing mechanism to size the frame to fit and conform to the endoluminal surface of the vessel in which the instrument is deployed.

Figure 2A:
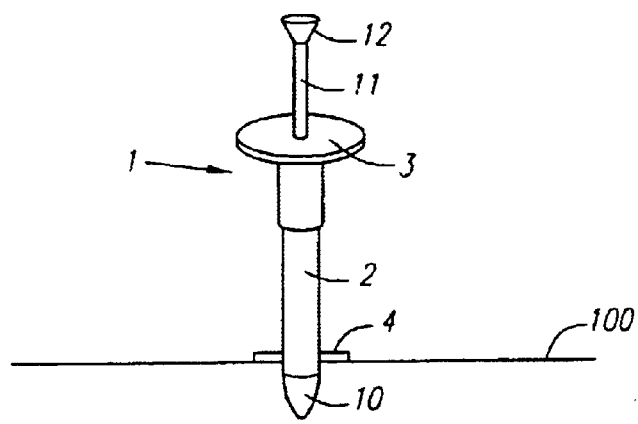
FIG. 2A depicts the device of FIG. 1A inserted in a blood vessel.
Figure 2B:
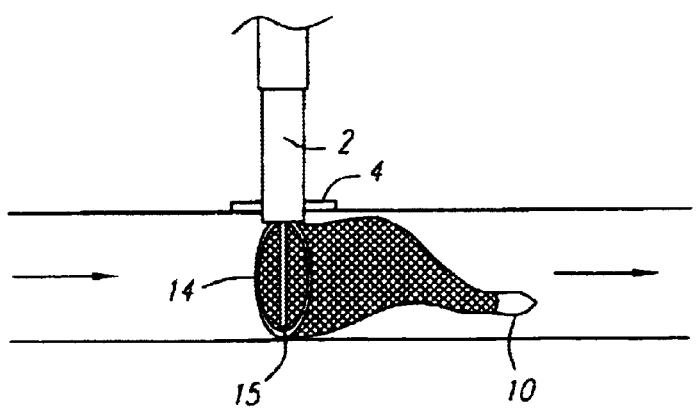
FIG. 2B depicts the device of FIG. 2A having the filter deployed in the blood vessel.

The filter as described herein will find use in any procedure for which distal embolization presents a complication. Illustrative procedures include cardiopulmonary bypass, CABG, valve repair, abdominal aortic aneurysm repair, carotid endarterectomy, carotid stenting, and carotid angioplasty. In use, an incision is made in the vessel where filter protection is desired, e.g., the ascending aorta for cardiopulmonary bypass, a coronary artery bypass grafting, or valve repair procedures, the abdominal aorta or femoral arteries for aortic aneurysm repair, the common carotid artery or internal carotid artery for carotid procedures. Obturator tip 10 is advanced atraumatically through the incision into the vessel as depicted in FIG. 2A. Suture flange 4 is secured to the wall of vessel 100. While holding handle 3, the operator depresses elongate member 11 by pushing on plug 12, much like the plunger of a syringe. This action causes obturator 10 to disengage from distal end 5 of tubular member 2. Filter 13 advances beyond distal end 5 and deploys within vessel 100 as shown in FIG. 2B. Expansion frame 14 and cantilever 15 ensure proper expansion of the filter into contact with the endoluminal surface of the vessel. The vessel, e.g., aorta, aorta is then cross-clamped or occluded upstream of the filter which catches dislodged debris. The surgeon then proceeds with the CABG or other desired procedure. Embolic materials, e.g., atheromatous plaque, calcium, thrombus, and tissue debris, are captured by the filter.

After the operative procedure is completed, the operator pulls back on plug 12 while holding handle 3. Filter 13, expansion frame 14, and cantilever beam 15 are thereby retracted into tubular member 2. Obturator tip 10 is pulled into engagement with distal end 5 of tubular member 2. The suture flange is released, and the device with the captured embolic debris is removed from the vessel.

Figure 3A:
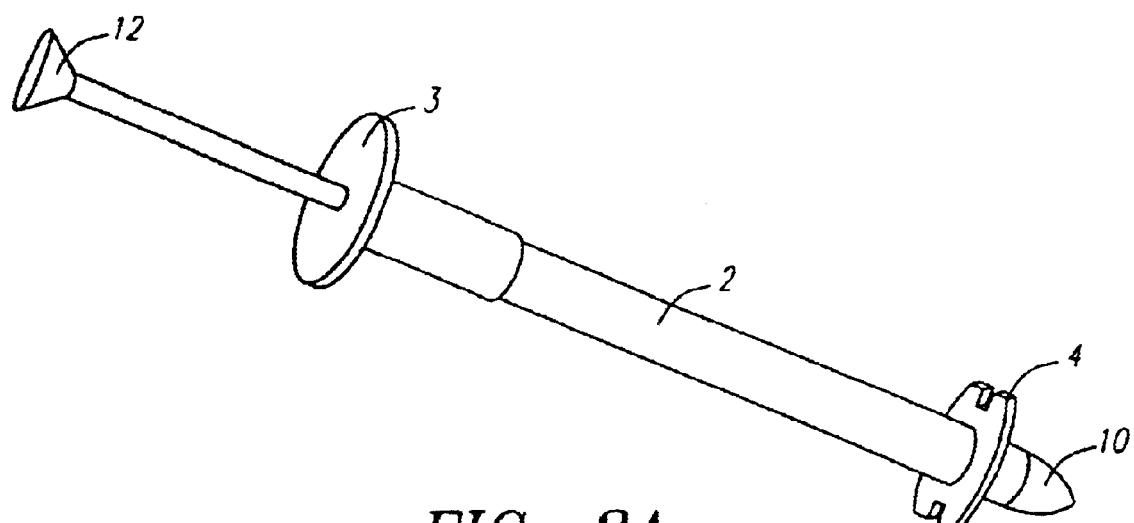
FIG. 3A depicts another embodiment of the device having a rounded obturator tip.
Figure 3B:
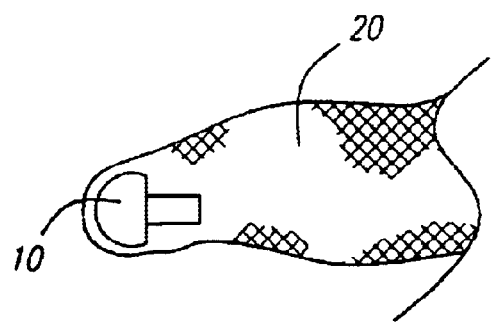
FIG. 3B depicts a filter mesh covering the obturator tip of FIG. 3A.
Figure 3C:
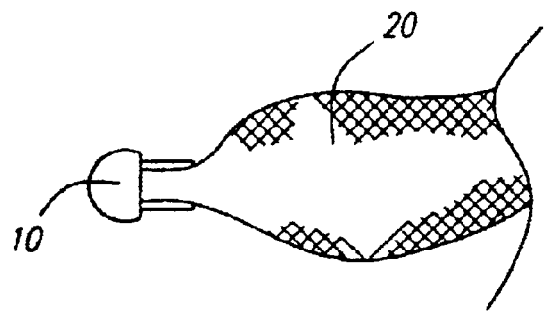
FIG. 3C depicts a filter mesh inserted inside the obturator tip of FIG. 3A

Another embodiment of the medical device having rounded obturator tip 10 is depicted in FIG. 3A. Filter mesh 20 may be disposed around tip 10 as shown in FIG. 3B. Alternatively, mesh 20 may be insert molded into tip 10 using thermoplastic polymer, silicone, or urethane as shown in FIG. 3C.

Figure 4A:
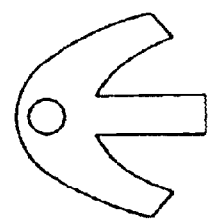
FIG. 4A depicts another embodiment of the device having a star-shaped obturator tip.
Figure 4B:
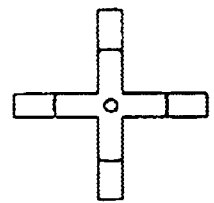
FIG. 4B depicts an end view of the obturator tip of FIG. 4A when laid flat.
Figure 4C:
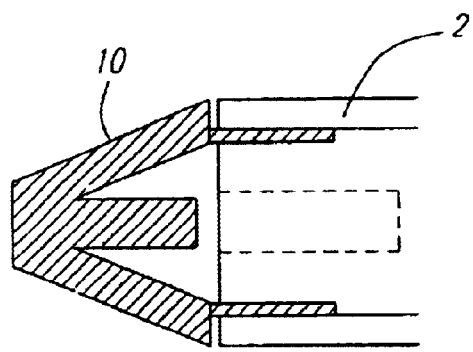
FIG. 4C depicts a lateral view of the obturator tip of FIG. 4A having a filter mesh attached.

FIGS. 4A, 4B, and 4C depict another embodiment of the obturator tip having a star shape. In FIG. 4C, obturator tip 10 is seated against the distal end of elongate tubular member 2. The mesh may be glued or molded onto the tip, or inserted onto the tip by two part heat staked inside and outside.

Figure 5:
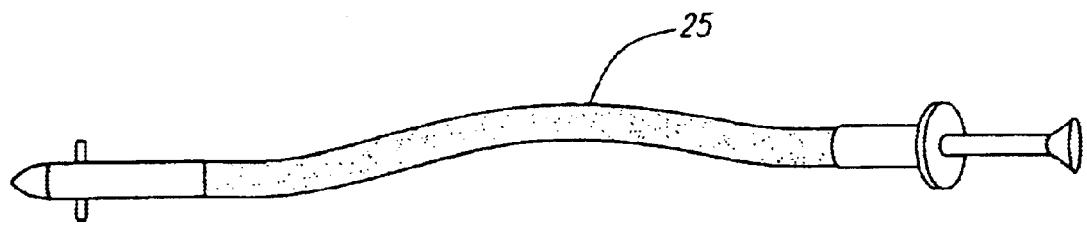
FIG. 5 depicts another embodiment of the device having a filter carried by a flexible elongate tubular member.

Another embodiment of the device having flexible elongate tubular member 25 is depicted in FIG. 5. This design allows the operator to manipulate the device in limited surgical space.

Figure 6A:
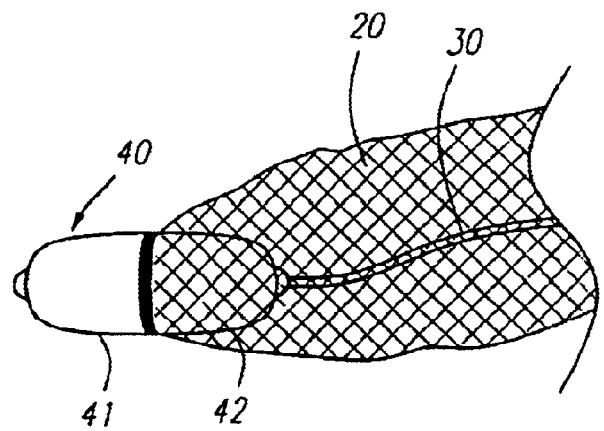
FIG. 6A depicts another embodiment of the obturator tip having an olive shape.
Figure 6B:
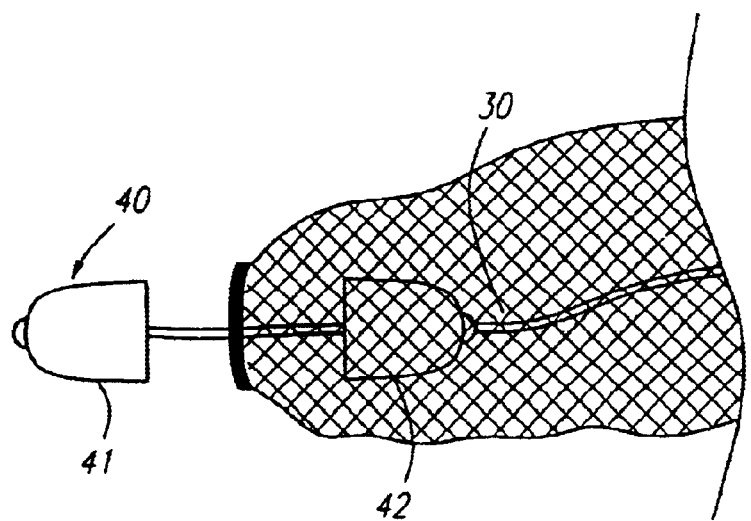
FIG. 6B depicts a wire attached to the olive obturator tip of FIG. 6A.

FIGS. 6A and 6B depict another embodiment of the obturator tip having an olive shape. Mesh 20 is disposed about the tip at a mid-region. Olive tip 40 comprises proximal section 42, positioned inside mesh 20, and distal section 41, positioned outside mesh 20. Safety wire 30 is attached at a proximal end of section 41 and continues proximally through section 42 as shown in FIG. 6B. The olive-shaped tip and the attached safety wire facilitate re-placement of the tip against the distal end of the elongate tubular member, minimize movement of the filter from blood flow, and reduce areas where blood may pool around the filter.

The overall length of the device 1 will generally be approximately between 10 and 20 centimeters, preferably approximately 12 to 15 centimeters. The outer diameter of tubular member 2 will generally be approximately between 5 and 10 millimeters, preferably approximately 6 and 7 millimeters. The diameter of the filter when expanded will vary depending on the vessel of use. For use in the aorta, the filter will expand to an endoluminal diameter of approximately 2.5 centimeters. The foregoing ranges are set forth solely for the purpose of illustrating typical device dimensions. The actual dimensions of a device constructed according to the principles of the present invention may obviously vary outside of the listed ranges without departing from the principles disclosed herein.

Although the foregoing invention has, for purposes of clarity of understanding, been described in some detail by way of illustration and example, it will be obvious that certain changes and modifications may be practiced which will still fall within the scope of the appended claims. It will also be understood that each feature of each embodiment discussed herein and of each reference cited herein, can be used in combination with the features of any other embodiment.

What is claimed is:

1. A medical device for open surgery, comprising:
   an elongate member having a proximal end and a distal end;
   an elongate tubular member having a proximal end, a distal end, and a lumen therebetween adapted to receive the elongate member;
   a filter slideably received within the lumen of the elongate tubular member, the filter having a generally conical shape having a base and an apex, the base being coupled to the elongate member, wherein an axis of the filter extends perpendicular to an axis of the elongate member; and
   an obturator tip carried by the filter at the apex of the filter and shaped to rest against the distal end of the elongate tubular member when the filter is within the lumen of the elongate tubular member.

2. The medical device of claim 1, wherein the filter is advanced distally beyond the distal end of the elongate tubular member after the device is inserted into a vessel.

3. The medical device of claim 1, wherein the obturator tip is olive-shaped.

4. The medical device of claim 1, wherein the filter comprises an expansion frame and a filter mesh attached to the expansion frame.

5. The medical device of claim 4, wherein the expansion frame is attached to the elongate member that extends through the lumen of the elongate tubular member.

6. The medical device of claim 4, wherein the expansion frame comprises a generally circular ring of a flexible material.

7. The medical device of claim 6, further comprising a cantilever beam that bisects the generally circular ring and attaches to the ring at a distal end.

8. The medical device of claim 1, wherein the filter comprises a generally conical mesh.

9. The medical device of claim 8, wherein the obturator tip is attached at the apex of the conical mesh.

10. The medical device of claim 1, further comprising a suture flange at a distal region of the elongate tubular member.

11. The medical device of claim 1, further comprising a hemostatic valve at the proximal end of the elongate tubular member.

12. A method for open surgery, comprising the steps of:
    providing an elongate member having a proximal end and a distal end, an elongate tubular member having a proximal end, a distal end, and a lumen adapted to receive the elongate member, a filter slideably received within the lumen, wherein the filter has a generally conical shape having a base and an apex, the base being coupled to the elongate member, and wherein an axis of the filter extends perpendicularly to an axis of the elongate member, and an obturator tip carried by the filter at the apex of the filter;
    inserting the obturator tip and distal end of the elongate tubular member into a vessel;
    advancing the filter and obturator tip beyond the distal end of the elongate tubular member; and
    deploying the filter in the vessel.

13. The method of claim 12, further comprising the step of withdrawing the filter into the lumen of the elongate tubular member so that the obturator tip rests against the distal end of the elongate tubular member.

14. The method of claim 13, further comprising the step of removing the medical device from the vessel.

15. The method of claim 12, wherein the vessel is an artery.

16. The method of claim 12, wherein the vessel is the aorta.

17. The method of claim 12, wherein the vessel is the ascending aorta.

18. The method of claim 12, wherein the vessel is the descending aorta.

19. The method of claim 12, wherein the vessel is the abdominal aorta.

20. The method of claim 12, wherein the vessel is the carotid artery.

21. The method of claim 12, further comprising the step of clamping the vessel upstream of the filter.

22. The method of claim 12, further comprising the step of performing cardiopulmonary bypass.

23. The method of claim 12, further comprising the step of installing a graft upstream of the filter to repair an abdominal aortic aneurysm.

24. The method of claim 12, further comprising the step of performing surgery on the vessel upstream of the filter.

* * * * *

UNITED STATES PATENT AND TRADEMARK OFFICE
CERTIFICATE OF CORRECTION

PATENT NO. : 6,790,219 B1
DATED : September 14, 2004
INVENTOR(S) : Richard O. Murphy It is certified that error appears in the above-identified patent and that said Letters Patent is hereby corrected as shown below:

Column 1,
Line 49, after "off pump" please delete "stemotomy" and insert -- sternotomy. --

Column 2,
Line 6, after "provided for" please delete "a traumatic" and insert -- atraumatic. --

Signed and Sealed this

Twenty-second Day of February, 2005

JON W. DUDAS
*Director of the United States Patent and Trademark Office*